(12) United States Patent
Marsolek et al.

(10) Patent No.: US 9,618,437 B2
(45) Date of Patent: Apr. 11, 2017

(54) SYSTEM AND METHOD FOR MONITORING WEAR OF A SCREED PLATE

(71) Applicant: Caterpillar Paving Products Inc., Brooklyn Park, MN (US)

(72) Inventors: John L. Marsolek, Watertown, MN (US); Mark C. Medeiros, Stouffville (CA); Dana W. Miller, Coon Rapids, MN (US)

(73) Assignee: Caterpillar Paving Products Inc., Brooklyn Park, MN (US)

( * ) Notice: Subject to any disclaimer, the term of this patent is extended or adjusted under 35 U.S.C. 154(b) by 159 days.

(21) Appl. No.: 14/698,898

(22) Filed: Apr. 29, 2015

(65) Prior Publication Data
US 2016/0320279 A1    Nov. 3, 2016

(51) Int. Cl.
G01N 3/56      (2006.01)
E01C 19/22     (2006.01)
E01C 19/48     (2006.01)
E01C 23/06     (2006.01)
E01C 21/00     (2006.01)
G01N 3/06      (2006.01)

(52) U.S. Cl.
CPC ............... *G01N 3/56* (2013.01); *E01C 19/22* (2013.01); *E01C 19/48* (2013.01); *E01C 21/00* (2013.01); *E01C 23/06* (2013.01); *G01N 3/066* (2013.01); *G01N 2203/0617* (2013.01); *G01N 2203/0664* (2013.01)

(58) Field of Classification Search
CPC   G01N 3/56; E01C 19/22; E01C 19/48; E01C 21/00; E01C 23/06
See application file for complete search history.

(56) References Cited

U.S. PATENT DOCUMENTS

| 4,865,487 | A  | * | 9/1989 | Lutz | E01C 19/48 404/118 |
|---|---|---|---|---|---|
| 5,752,783 | A | * | 5/1998 | Malone | E01C 19/006 404/104 |
| 6,890,125 | B1 | | 5/2005 | Calder et al. | |
| 8,764,342 | B1 | * | 7/2014 | Kopacz | E01C 19/30 37/381 |
| 2011/0123269 | A1 | * | 5/2011 | Lutz | E01C 19/42 404/118 |
| 2015/0003914 | A1 | * | 1/2015 | Steinhagen | E01C 19/48 404/118 |
| 2015/0267361 | A1 | * | 9/2015 | Horn | E01C 19/22 404/84.05 |

FOREIGN PATENT DOCUMENTS

RU   2380680 C1 *  1/2010
WO   2014026452     2/2014

* cited by examiner

*Primary Examiner* — Francis Gray

(57) ABSTRACT

A system for monitoring a wear of a screed plate of a paving machine is disclosed. The system includes a sensor located on the screed plate. The sensor generates signals indicative of the wear of the screed plate. The system further includes a controller coupled to the sensor. The controller receives signals from the sensor and determines the wear of the screed plate based on the received signals.

20 Claims, 4 Drawing Sheets

SYSTEM AND METHOD FOR MONITORING WEAR OF A SCREED PLATE

TECHNICAL FIELD

The present disclosure relates to a paving machine, and more particularly relates to a system and a method for monitoring a wear of a screed plate of the paving machine.

BACKGROUND

Paving machines are generally used for laying paving materials, such as asphalt, on a work surface. The paving machine includes a screed system disposed behind the paving machine to receive the paving material from a hopper and deposit the paving material on the work surface. The screed system includes a screed plate for levelling the paving material with respect to the work surface. Hence, during paving operation of the paving machine, the screed plate is in continuous contact with the paving material relative to the work surface. Prolonged contact of the screed plate with the paving material may cause wear of the screed plate. The wear in the screed plate may cause uneven levelling of the paving material on the work surface. Further, uneven wear across various locations on the screed plate may require replacement of the screed plate. Such replacement may delay a paving operation and decrease productivity of the pacing machine.

U.S. Pat. No. 5,752,783 (the '783 patent) discloses a paver having a radar screed control. The paver includes a screed alignment sensor disposed on extendable sections of a screed plate to track a reference corresponding with an edge of a surface to be paved. A radar device is used to measure deviation from the reference. The paver further includes a screed controller to receive signals from the screed alignment sensor to adjust the extendable sections base on the reference. However, the '783 patent does not consider adjusting a position of the screed plate and the extendable sections based on a wear of the screed plate.

SUMMARY OF THE DISCLOSURE

In one aspect of the present disclosure, a system for monitoring a wear of a screed plate of a paving machine is provided. The system includes a sensor located on the screed plate. The sensor is configured to generate signals indicative of the wear of the screed plate. The system further includes a controller communicably coupled to the sensor. The controller is configured to receive signals from the sensor and determine the wear of the screed plate based on the received signals.

In another aspect of the present disclosure, a paving machine is provided. The paving machine includes a frame and a screed plate movably coupled to the frame. The screed plate is configured to contact with a work surface. The paving machine further includes a system for monitoring a wear of the screed plate. The system incudes a plurality of sensors disposed at a plurality of locations on the screed plate. Each of the plurality of sensors is configured to generate signals indicative of the wear of the screed plate at a corresponding location of the plurality of locations on the screed plate. The system further incudes a controller communicably coupled to each of the plurality of sensors. The controller is configured to receive signals from each of the plurality of sensors and determine the wear of the screed plate based on the received signals.

In yet another aspect of the present disclosure, a method of monitoring a wear of a screed plate of a paving machine is provided. The method includes receiving signals from a sensor located on the screed plate and determining the wear of the screed plate based on the received signals. The method further includes moving the screed plate with reference to a work surface based on the determined wear.

Other features and aspects of this disclosure will be apparent from the following description and the accompanying drawings.

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts.

Figure 1:
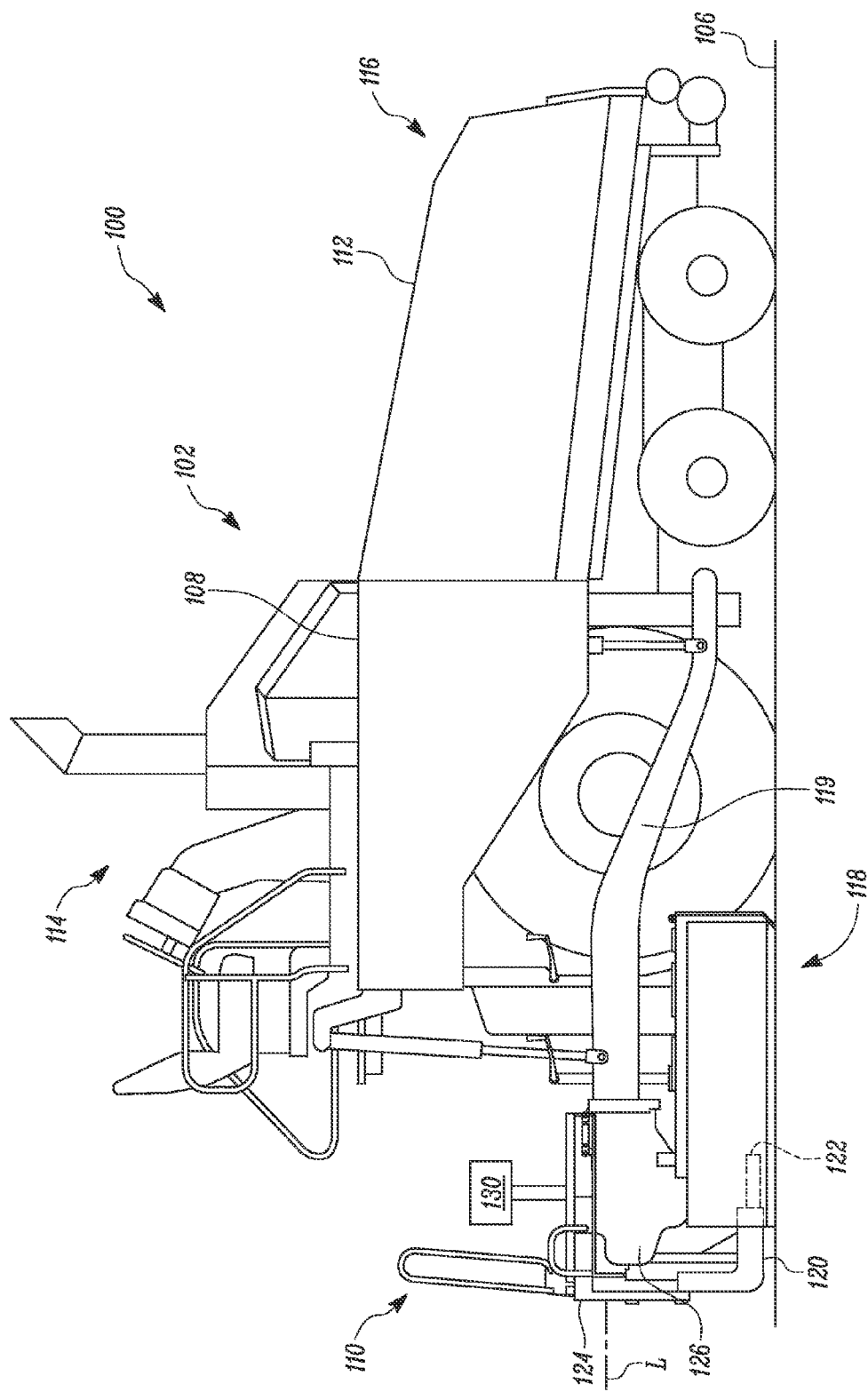
FIG. 1 is a side view of a paving machine, according to an embodiment of the present disclosure.

FIG. 1 illustrates a side view of a paving machine 100, according to an embodiment of the present disclosure. The paving machine 100 may be used for laying paving materials, such as asphalt, on various work surfaces such, as roadways. The paving machine 100 includes a tractor 102 to propel the paving machine 100. In the illustrated embodiment, the tractor 102 is a wheel type tractor. The wheel type tractor includes a plurality of wheels for providing traction to the tractor 102 with a work surface 106. In other embodiments, the tractor 102 may be a track type tractor that may include tracks to provide traction to the tractor 102 with the work surface 106. The paving machine 100 may further include an engine (not shown) for propelling the tractor 102 and a generator coupled to the engine. The generator may be configured to supply electric power to various electric components of the paving machine 100.

The tractor 102 includes a frame 108 configured to support various components of the paving machine 100 including, but not limited to, a screed system 110, a hopper 112 and an operator station 114. The hopper 112 is disposed adjacent to a front end 116 of the paving machine 100. The hopper 112 may be configured to receive the paving materials from a dump truck. The operator station 114 is disposed adjacent to a rear end 118 of the paving machine 100. The operator station 114 may include control levers and/or switches for an operator to control various operations, such as paving operation of the paving machine 100.

The screed system 110 is disposed adjacent to the rear end 118 of the paving machine 100 behind the operator station 114. Specifically, the screed system 110 is movably coupled to the frame 108 of the tractor 102 via a pair of arms 119. One of the pair of arms 119 is shown in FIG. 1. In various embodiments, the screed system 110 may be coupled to the frame 108 of the tractor 102 adjacent to the front end 116 of the paving machine 100. The screed system 110 may be configured to receive the paving material from the hopper 112 and deposit the asphalt on the work surface 106. The screed system 110 may be further configured to maintain a thickness for a layer of the deposited asphalt with reference to the work surface 106.

In an embodiment, the screed system 110 includes a screed plate 120 and a pair of extension plates 122. One of the pair of extension plates 122 is shown in FIG. 1. Each of the pair of extension plates 122 is disposed laterally with respect to the screed plate 120. The screed system 110 further includes a first support member 124 to support the screed plate 120 and a pair of second support members 126 to support the pair of extension plates 122. The screed plate 120 and the extension plates 122 are configured to contact with the work surface 106 to level the deposited paving material with respect to the work surface 106. The first support member 124 may be adjusted angularly about a longitudinal axis 'L' and may be moved up and down based on the work surface 106 to define the layer of the asphalt on the work surface 106. Each of the second support members 126 may also be adjusted about a respective longitudinal axis (not shown) parallel to the longitudinal axis 'L'. Further, the second support members 126 may be adjusted in a vertical direction and a lateral direction relative to the frame 108 and the work surface 106 to define the layer of the asphalt on the work surface 106.

The paving machine 100 further includes a system 130 for monitoring a wear (shown in FIG. 4) of the screed plate 120. The system 130 is also configured to monitor a wear of the pair of extension plates 122. The system 130 will be described in detail herein below. As the screed plate 120 and the pair of extension plates 122 are configured to contact with the work surface 106 during paving operation of the paving machine 100, the screed plate 120 and the extension plates 122 may experience a wear due to a prolonged operation of the paving machine 100. The system 130 is configured to determine the wear of the screed plate 120 and the extension plates 122 to take necessary action during the paving operation.

Figure 2:
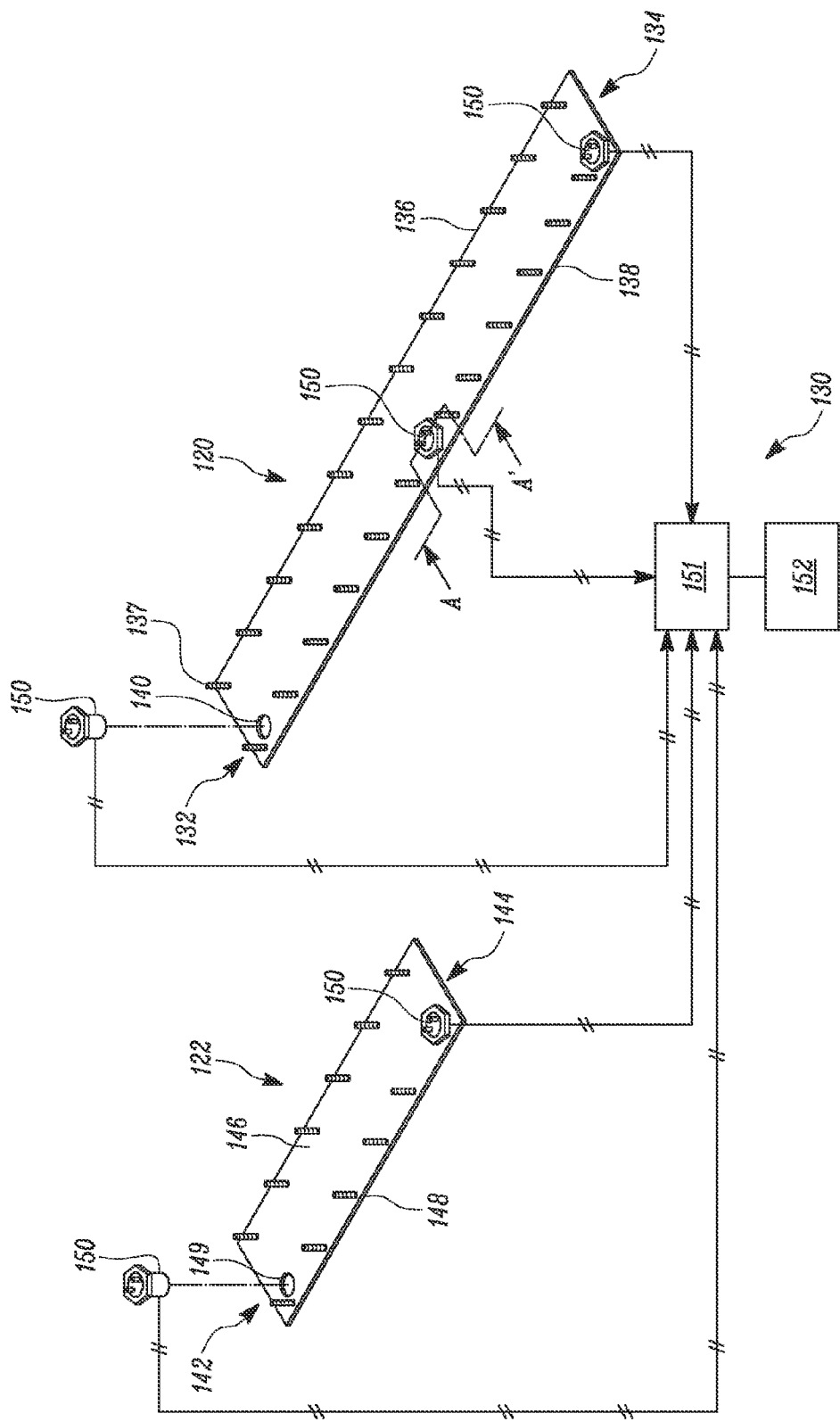
FIG. 2 is a perspective view of a screed plate and an extension plate of the paving machine, according to an embodiment of the present disclosure.

FIG. 2 is a perspective view of the screed plate 120 and the extension plate 122 of the paving machine 100, according to an embodiment of the present disclosure. One of the pair of extension plates 122 is shown in FIG. 2 for illustration of the present disclosure. The screed plate 120 is an elongate body having a first end 132 and a second end 134 distal to the first end 132. The screed plate 120 includes a top surface 136 and a bottom surface 138 distal to the top surface 136. The top surface 136 is configured to support heating elements (not shown) thereon. Further, the top surface 136 includes a plurality of fastening members 137 to couple the screed plate 120 to the first support member 124 of the screed system 110. The screed plate 120 further includes a plurality of through holes 140 extending between the top surface 136 and the bottom surface 138.

Similarly, the extension plate 122 includes a first end 142 and a second end 144. The second end 144 of the extension plate 122 may be disposed adjacent to the first end 132 of the screed plate 120. The extension plate 122 further includes a top surface 146 and a bottom surface 148. The top surface 146 may be configured to support heating elements (not shown) thereon. Further, the top surface 146 includes a plurality of fastening members 147 to couple the extension plate 122 to the second support member 126 of the screed system 110. The extension plate 122 further includes a plurality of through holes 149 extending between the top surface 146 and the bottom surface 148.

In an embodiment, the system 130 includes a sensor 150 located on the screed plate 120. Specifically, the sensor 150 is located within one of the through holes 140 defined in the screed plate 120. An exploded view of one of the plurality of sensors 150 is shown in FIG. 2 for illustration of the present disclosure. In other embodiments, the system 130 includes a plurality of sensors 150 disposed at a plurality of locations on the screed plate 120. Each of the plurality of sensors 150 is located within each of the plurality of through holes 140. Each of the sensors 150 is further configured to generate signals indicative of the wear of the screed plate 120 at a corresponding location of the plurality locations on the screed plate 120. In the illustrated embodiment, the sensor 150 is a sacrificial sensor. Portions of the sensor 150 may be removed based on varying degrees of wear of the screed plate 120. This enables the sensor 150 to generate signals indicative of the degree of the wear of the screed plate 120. The sensor 150 will be described in detail later with reference to FIGS. 3 and 4. In various embodiments, non-sacrificial type of sensors may also be used to determine the wear of the screed plate 120.

Similarly, another plurality of sensors 150 is located on the extension plate 122. Each of the plurality of sensors 150, located on the extension plate 122, is also be configured to generate signals indicative of the wear of the extension plate 122. Specifically, each of the plurality of sensors 150 is located within each of the through holes 149 of the extension plate 122.

A location of each of the sensors 150 and number of sensors 150 disposed on the screed plate 120 may be determined based on various parameters including, but not limited to, a type of the sensor 150, such as sacrificial or non-sacrificial, a type of a wear output that is to be generated, a length and a width of the screed plate 120, a thickness of the screed plate 120 defined between the top surface 136 and the bottom surface 138 and a design specification of the sensor 150. Aforesaid parameters may also be considered for defining a location and a number of sensors 150 for the pair of extension plates 122.

The system 130 further includes a controller 151 communicably coupled to each of the sensors 150. The controller 151 is configured to receive signals, indicative of the wear of the screed plate 120, generated by each of the sensors 150. In an embodiment, the controller 151 may be located in the screed system 110. Further, each of the sensors 150 may be connected to the controller 151 via one or more wires as shown in FIG. 2. In another embodiment, the controller 151 may be located in the tractor 102 of the paving machine 100. The controller 151 is further configured to determine the wear of the screed plate 120 based on the received signals.

The system 130 further includes a display device 152 configured to display an output indicative of the wear determined based on the received signals. In an embodiment, the display device 152 may be located within the paving machine 100. In an example, the paving machine 100 may include a pair of display devices 152 located in the screed system 110 and a display device 152 located in the operator station 114. In another example, the display device 152 may be located remotely with respect the paving machine 100. In such cases, the controller 151 may be communicably coupled to each of the display devices 152 to display the output indicative of the wear of the screed plate 120. In another embodiment, the display device 152 may be part of the controller 151. In various embodiments, the controller 151 may be configured to notify the operator based on the wear of the screed plate 120 via various output devices, such as a sound generating device.

Figure 3:
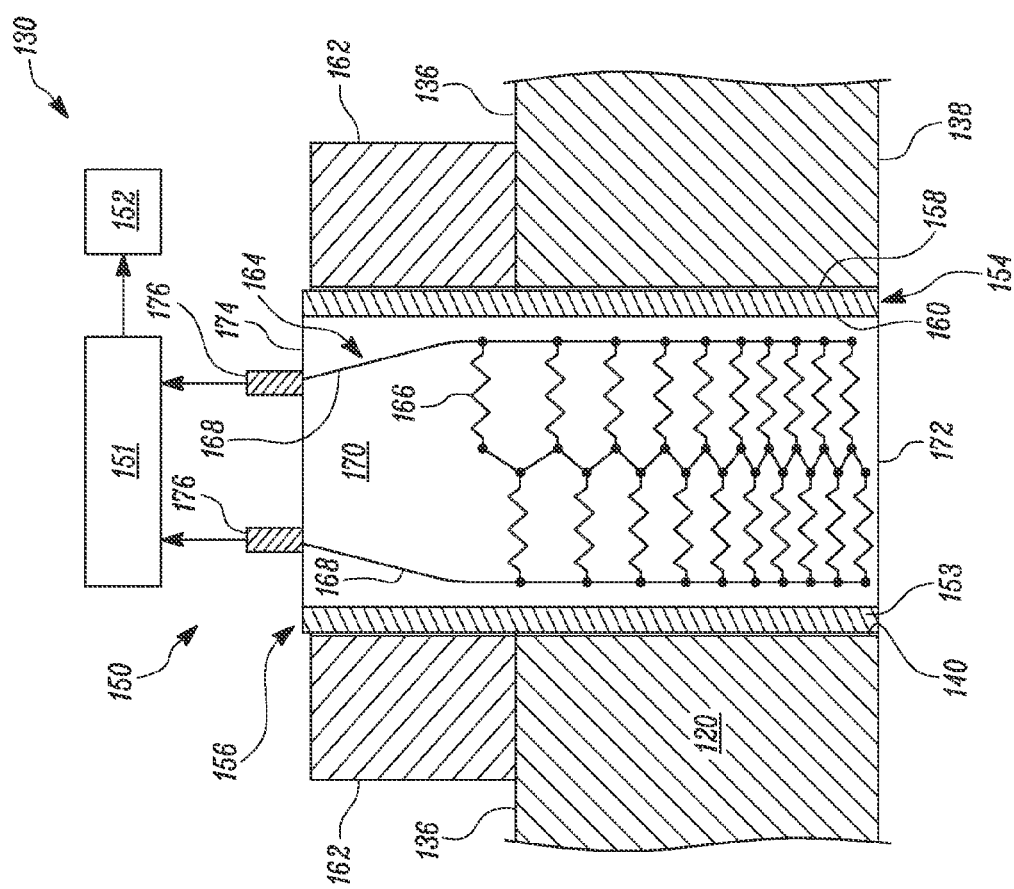
FIG. 3 is a partial sectional view taken along line A-A' of the screed plate of FIG. 2, according to an embodiment of the present disclosure.

FIG. 3 illustrates a partial sectional view taken along line A-A' of the screed plate 120 of FIG. 2, according to an embodiment of the present disclosure. The sensor 150 of the system 130 includes a hollow body 153 defining a first end 154 and a second end 156 distal to the first end 154. The first end 154 of the hollow body 153 is located adjacent to the bottom surface 138 of the screed plate 120. Thus, the first end 154 of the hollow body 153 is aligned with the bottom surface 138 of the screed plate 120. Further, the second end 156 of the hollow body 153 is configured to project from the through hole 140 above the top surface 136 of the screed plate 120. The hollow body 153 further defines a length extending between the first end 154 and the second end 156. The length of the hollow body 153 is greater than the thickness of the screed plate 120. The hollow body 153 further defines an outer surface 158 and an inner surface 160. In an embodiment, threads (not shown) may be defined on the outer surface 158 of the hollow body 153 to engage with threads (not shown) defined on an inner surface of the through hole 140.

A portion of the hollow body 153, projecting above the top surface 136 of the screed plate 120, is engaged with a nut 162 to retain the hollow body 153 within the through hole 140. In an embodiment, the outer surface 158 of the portion of the hollow body 153 may be provided with threads to engage with the nut 162. In other embodiments, the hollow body 153 may be retained within the through hole 140 via a lock plate or any other device for securing the hollow body 153 within the through hole 140.

The sensor 150 further includes a resistor network 164 disposed within the hollow body 153. The resistor network 164 includes a plurality of resistors 166 connected between a pair of electric leads 168. In an example, the pair of electric leads 168 may include a positive lead and a negative lead. In an embodiment, a gap defined between two adjacent resistors 166 may decrease progressively towards the first end 154 of the hollow body 153. In another embodiment, the gap between two adjacent resistors 166 may be kept same throughout the resistor network 164. Further, in one embodiment, each of the resistors 166 may have an equal resistance value. In another embodiment, each of the resistors 166 may have a different resistance value.

The resistor network 164 may be encapsulated within the hollow body 153 by a potting material 170. The potting material 170 may form a solid structure along with the resistor network 164 within the hollow body 153. The potting material 170 may further define a first surface 172 adjacent to the first end 154 of the hollow body 153 and a second surface 174 adjacent to the second end 156 of the hollow body 153. In an example, the potting material 170 may be selected from one of an epoxy resin, a polyester, a polyurethane, a silicone elastomer, a ceramic and a combination thereof. Moreover, the potting material 170 may be electrically insulating, thermally conductive, shock absorbent, moisture resistant, fatigue resistant and chemically resistant.

The sensor 150 further includes a pair of pins 176 disposed adjacent to the second end 156 of the hollow body 153. Each of the pair of pins 176 is coupled to each of the pair of electric leads 168. In an embodiment, each of the pair of pins 176 may be disposed on the second surface 174 defined by the potting material 170. In other embodiments, the pair of pins 176 may be disposed at any location adjacent to the second end 156 of the hollow body 153. The pair of pins 176 is further configured to be communicably coupled with the controller 151 to send signals indicative of the wear of the screed plate 120.

Construction of the sensor 150, as described above, is illustrative in nature, and various alternative sensors may be located on the screed plate 120 to determine the wear of the screed plate 120.

Figure 4:
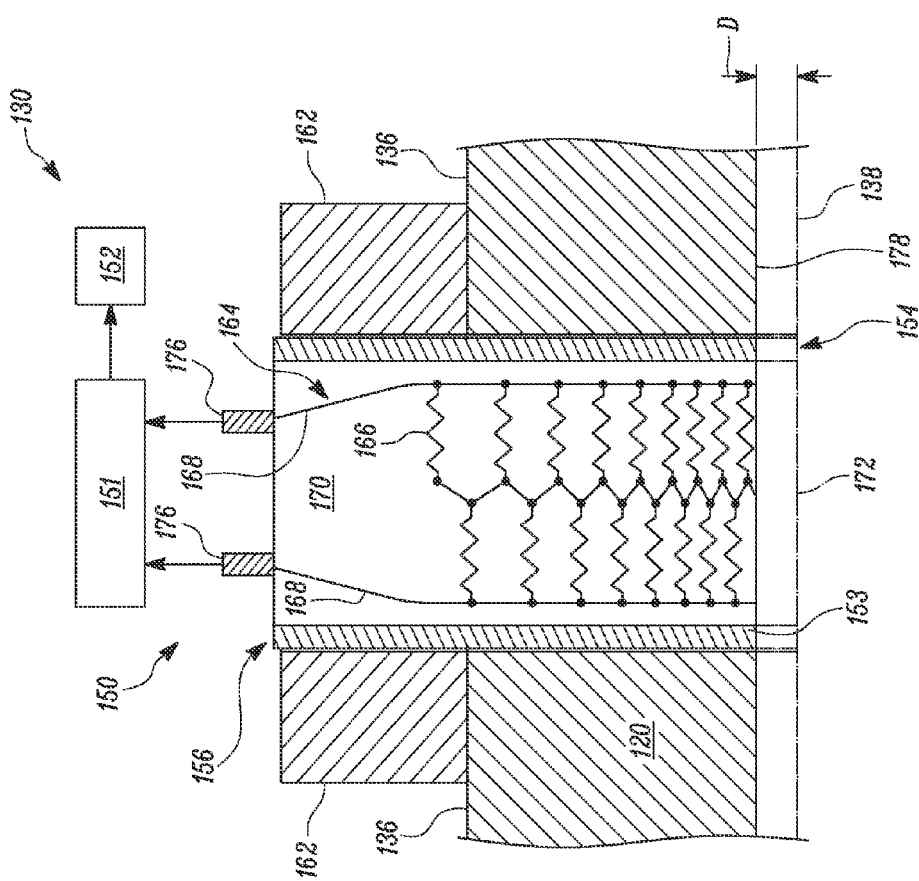
FIG. 4 is a partial sectional view of the screed plate showing an exemplary wear profile thereof.

FIG. 4 illustrates a partial sectional view of the screed plate 120 showing an exemplary wear profile 178 thereof. Due to prolonged operation of the paving machine 100, the bottom surface 138 of the screed plate 120 may tend to undergo wear due to a contact between the screed plate 120 and the paving material laid on the work surface 106. The wear profile 178 of the screed plate 120 shown in FIG. 4 is for illustrative purposes only. As the bottom surface 138 of the screed plate 120 wears, the first end 154 of the hollow body 153 and the first surface 172 defined by the potting material 170 also undergo wear. Such wear of the bottom surface 138 of the screed plate 120 and the first end 154 of the hollow body 153 causes progressive removal of the plurality of electric resistors 166 of the resistor network 164. The progressive removal of the plurality of electric resistors 166 is based on a depth 'D' of the wear of the screed plate 120 with reference to the bottom surface 138. As the electric resistors 166 are progressively removed from the resistor network 164, an electric resistance measured between the pair of electric leads 168 may change. A change in the electrical resistance between the pair of electric leads 168 may be based on including, but not limited to, the number of electric resistors 166 removed from the resistor network 164, resistance value of the electric resistors 166 and the depth 'D' of the wear of the screed plate 120.

Thus, the sensor 150 generates signals indicative of the wear of the screed plate 120 based on the change in the electrical resistance of the resistor network 164. The controller 151 coupled to the sensor 150 receives the signals from the sensor 150. The controller 151 further determines the wear of the screed plate 120 based on the signals received from the sensor 150. In the illustrated embodiment, the controller 151 is configured to receive signals from each of the plurality of sensors 150 located on the corresponding location of the plurality of locations on the screed plate 120. Each of the plurality of sensors 150 is configured to generate signals indicative of the wear of the screed plate 120 corresponding to the location of each of the plurality of sensors 150 on the screed plate 120. The controller 151 communicated with each of the plurality of sensors 150 is further configured to determine the wear profile 178 of the screed plate 120 based on the bottom surface 138 of the screed plate 120 such that the depth 'D' of wear of the screed plate 120 may be determined with respect to the bottom surface 138. In other embodiments, the top surface 136 or any of side surfaces of the screed plate 120 may be defined as a reference surface to determine a magnitude of the wear with respect to the top surface 136 or the side surface, respectively.

The controller 151 further communicates the wear profile 178 of the screed plate 120 to the display device 152. In an embodiment, the controller 151 may be configured to determine the wear of the screed plate 120 at the corresponding location of the plurality of locations on the screed plate 120. In such a case, the magnitude of the wear of the screed plate 120 at the corresponding location on the screed plate 120 may be displayed in the display device 152. In another embodiment, the controller 151 may determine the wear profile 178 based on the signals received from the plurality of sensors 150. The wear profile 178 of the screed plate 120 may be displayed in the display device 152 in two dimensions or three dimensions. Similarly, the controller 151 receives signals from the plurality of sensors 150 disposed on the extension plates 122 to determine wear of the extension plates 122. In various embodiments, the wear determined by the controller 151 may be communicated to a service personnel located remotely with respect to the machine via a wireless network.

The controller 151 may be further configured to move the screed plate 120 with reference to the work surface 106 based on the determined wear. In an embodiment, a position of the screed plate 120 with respect to the work surface 106 may be adjusted based on an input from an operator. The controller 151 may be configured to receive the input from the operator. Thus, the operator may adjust the position of the screed plate 120 based on the wear of the screed plate 120. In another embodiment, the controller 151 may be configured to adjust the position of the screed plate 120 based on the wear of the screed plate 120 without any manual intervention. Further, the controller 151 may be configured to move the extension plates 122 with reference to the work surface 106 based on the wear of the extension plates 122.

INDUSTRIAL APPLICABILITY

The present disclosure relates to the system 130 for monitoring the wear of the screed plate 120 of the paving machine 100. The sensor 150, coupled to the screed plate 120 of the paving machine 100, generates signals indicative of the wear of the screed plate 120. The signal from the sensor 150 is communicated with the controller 151. The controller 151 further determines the wear of the screed plate 120 based on the received signals. Hence, the positon of the screed plate 120 with respect to the work surface 106 may be adjusted based on the wear of the screed plate 120.

A method of monitoring the wear of the screed plate 120 and the extension plates 122 is described herein below, according to an embodiment of the present disclosure. The method includes receiving signals from the sensor 150 located on the screed plate 120. The signals indicative of the wear of the screed plate 120 may be generated by each of the sensors 150 based on the change in electrical resistance of the resistor network 164. The controller 151, disposed in communication with each of the plurality of sensors 150, receives the signals indicative of the wear of the screed plate 120.

The method further includes determining the wear of the screed plate 120 based on the received signals. The controller 151 determines the wear of the screed plate 120 at the corresponding location of the plurality of locations on the screed plate 120. In another embodiment, the controller 151 determines the wear profile 178 with respect to the bottom surface 138 of the screed plate 120 based on the signals received from the plurality of sensors 150.

The method further includes moving the screed plate 120 with reference to the work surface 106 based on the determined wear. The operator may adjust the position of the screed plate 120 with respect to the work surface 106 based on the wear determined by the controller 151. Thus, the screed plate 120 may be moved to adjust angle of attack on the screed plate 120 over a period of time to maximize a life of the screed plate 120. Moreover, occurrence of wear in the screed plate 120 may be minimized.

By determining the wear of the screed plate 120, unevenness in the thickness of the layer of asphalt that may be caused due to the wear of the screed plate 120 and the extension plates 122 may be eliminated. Further, replacement of the screed plate 120 and the extension plates 122 may be planned in advance to improve productivity and efficiency of the paving operation. Also, communication of the wear of the screed plate 120 to the service personnel located remotely may help the operator to plan replacement of the screed plate 120.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A system for monitoring a wear of a screed plate of a paving machine, the system comprising:
   a sensor located on the screed plate, the sensor configured to generate signals indicative of the wear of the screed plate; and
   a controller communicably coupled to the sensor, the controller configured to:
      receive signals from the sensor; and
      determine the wear of the screed plate based on the received signals.

2. The system of claim 1 further comprising a plurality of sensors disposed at a plurality of locations on the screed plate, wherein each of the plurality of sensors is configured to generate signals indicative of the wear of the screed plate at a corresponding location of each of the plurality of locations.

3. The system of claim 2, wherein the controller is communicably coupled to the plurality of sensors, and wherein the controller is further configured to determine a wear profile based on the wear determined at the plurality of locations on the screed plate.

4. The system of claim 1, wherein the controller is further configured to communicate the wear of the screed plate to a display device.

5. The system of claim 1, wherein the sensor comprises a resistor network communicably coupled with the controller, and wherein an electrical resistance of the resistor network varies based on an extent of the wear of the screed plate.

6. The system of claim 5, wherein the sensor further comprises a hollow body at least partly received in a through hole defined in the screed plate, and wherein the resistor network is disposed within the hollow body.

7. The system of claim 6, wherein a first end of the hollow body is located adjacent to a bottom surface of the screed plate, and wherein a second end of the hollow body projects from the through hole of the screed plate and is configured to engage with a nut to retain the hollow body within the through hole.

8. The system of claim 7, wherein the resistor network comprises a plurality of electric resistors connected with each other, wherein the wear of the screed plate at the bottom surface thereof causes progressive removal of the plurality of electric resistors, and wherein the progressive removal of the plurality of electric resistors is based on a depth of the wear of the bottom surface.

9. The system of claim 1, wherein the controller is further configured to move the screed plate with reference to a work surface based on the determined wear of the screed plate.

10. A paving machine comprising:
    a frame;
    a screed plate movably coupled to the frame, the screed plate configured to contact with a work surface; and a system for monitoring a wear of the screed plate, the system comprising:
  a plurality of sensors disposed at a plurality of locations on the screed plate, each of the plurality of sensors configured to generate signals indicative of the wear of the screed plate at a corresponding location of the plurality of locations on the screed plate; and
  a controller communicably coupled to each of the plurality of sensors, the controller configured to:
    receive signals from each of the plurality of sensors; and
    determine the wear of the screed plate based on the received signals.

11. The paving machine of claim 10, wherein the controller is further configured to determine a wear profile based on the wear determined at the corresponding location of the plurality of locations on the screed plate.

12. The paving machine of claim 10, wherein the controller is further configured to communicate the wear of the screed plate to a display device.

13. The paving machine of claim 10 further comprising another plurality of sensors located on an extension plate associated with the screed plate, wherein each of the another plurality of sensors is configured to generate signals indicative of a wear of the extension plate, and wherein the extension plate is movably disposed proximate to the screed plate.

14. The paving machine of claim 10, wherein each of the sensors comprises a resistor network communicably coupled with the controller, and wherein an electrical resistance of the resistor network varies based on an extent of the wear of the screed plate.

15. The paving machine of claim 14, wherein the sensor further comprises a hollow body at least partly received in a through hole defined in the screed plate, and wherein the resistor network is disposed within the hollow body.

16. The paving machine of claim 15, wherein a first end of the hollow body is located adjacent to a bottom surface of the screed plate, and wherein a second end of the hollow body projects from the through hole of the screed plate and is configured to engage with a nut to retain the hollow body within the through hole.

17. The paving machine of claim 16, wherein the resistor network comprises a plurality of electric resistors connected with each other, wherein the wear of the screed plate at the bottom surface thereof causes progressive removal of the plurality of electric resistors, and wherein the progressive removal of the plurality of electric resistors is based on a depth of the wear of the bottom surface.

18. A method of monitoring a wear of a screed plate of a paving machine, the method comprising:
  receiving signals from a sensor located on the screed plate;
  determining the wear of the screed plate based on the received signals; and
  moving the screed plate with reference to a work surface based on the determined wear.

19. The method of claim 18, wherein a plurality of sensors is disposed at a plurality of locations on the screed plate, and wherein the method further comprising determining a wear profile of the screed plate based on signals received from the plurality of sensors.

20. The method of claim 18 further comprising communicating the wear of the screed plate to a display device.

* * * * *